United States Patent
Gerlach et al.

(10) Patent No.: US 7,179,260 B2
(45) Date of Patent: Feb. 20, 2007

(54) BONE PLATES AND BONE PLATE ASSEMBLIES

(75) Inventors: Darin Gerlach, Cordova, TN (US); Anthony James, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 387 days.

(21) Appl. No.: 10/673,833

(22) Filed: Sep. 29, 2003

(65) Prior Publication Data

US 2005/0070904 A1  Mar. 31, 2005

(51) Int. Cl.
*A61B 17/56* (2006.01)
*A61B 17/58* (2006.01)

(52) U.S. Cl. ............................ 606/69; 606/73

(58) Field of Classification Search ............... 606/69, 606/61, 70, 71, 72, 73
See application file for complete search history.

(56) References Cited

U.S. PATENT DOCUMENTS

| | | |
|---|---|---|
| 576,631 A | 1/1897 | Brooks |
| 902,040 A | 10/1908 | Wyckoff |
| 2,501,978 A | 5/1950 | Wichman |
| RE31,628 E | 7/1984 | Allgower et al. |
| 4,484,570 A | 11/1984 | Sutter et al. |
| 5,085,660 A | 2/1992 | Lin |
| 5,324,291 A | 6/1994 | Ries et al. |
| 5,395,374 A | 3/1995 | Miller et al. |
| 5,415,658 A | 5/1995 | Kipela et al. |
| 5,470,333 A | 11/1995 | Ray |
| 5,527,310 A | 6/1996 | Cole et al. |
| 5,536,127 A | 7/1996 | Pennig |
| 5,601,553 A | 2/1997 | Trebing et al. |
| 5,665,088 A | 9/1997 | Gil et al. |
| 5,676,667 A | 10/1997 | Hausman |
| 5,702,399 A | 12/1997 | Kipela et al. |
| 5,709,686 A | 1/1998 | Talos et al. |
| 5,954,722 A | 9/1999 | Bono |
| 5,964,769 A | 10/1999 | Wagner et al. |
| 5,968,046 A | 10/1999 | Castleman |

(Continued)

FOREIGN PATENT DOCUMENTS

DE  43 43 117 A1  9/1995

(Continued)

OTHER PUBLICATIONS

Baumgaertel, et al., "Fracture healing in biological plate osteosynthesis," *Injury*, 29(Supp. 3):S-C3-S-C6 (1998).

(Continued)

*Primary Examiner*—Pedro Philogene
(74) *Attorney, Agent, or Firm*—Kilpatrick Stockton LLP

(57) ABSTRACT

Bone plates with an upper surface, a bone contacting surface, and at least one hole extending through the upper and bone contact surfaces are disclosed. A hole interchangeably accepts a compression screw for compression of a fracture and a locking screw that threads into the bone plate.

11 Claims, 15 Drawing Sheets

U.S. PATENT DOCUMENTS

| | | | |
|---|---|---|---|
| 6,053,921 | A | 4/2000 | Wagner et al. |
| 6,129,730 | A | 10/2000 | Bono et al. |
| 6,176,861 | B1 | 1/2001 | Bernstein et al. |
| 6,193,721 | B1 | 2/2001 | Michelson |
| 6,206,881 | B1 * | 3/2001 | Frigg et al. .................... 606/69 |
| 6,235,033 | B1 | 5/2001 | Brace et al. |
| 6,306,136 | B1 | 10/2001 | Baccelli |
| 6,306,140 | B1 | 10/2001 | Siddiqui |
| 6,322,562 | B1 * | 11/2001 | Wolter .......................... 606/69 |
| 6,355,043 | B1 | 3/2002 | Adam |
| 6,358,250 | B1 | 3/2002 | Orbay |
| 6,361,537 | B1 | 3/2002 | Anderson |
| 6,391,030 | B1 | 5/2002 | Wagner et al. |
| 6,413,259 | B1 | 7/2002 | Lyons et al. |
| 6,428,542 | B1 | 8/2002 | Michelson |
| 6,440,135 | B2 | 8/2002 | Orbay et al. |
| 6,454,769 | B2 | 9/2002 | Wagner et al. |
| 6,506,191 | B1 | 1/2003 | Joos |
| 6,520,965 | B2 | 2/2003 | Chervitz et al. |
| 6,623,486 | B1 * | 9/2003 | Weaver et al. ................ 606/69 |
| 6,682,533 | B1 | 1/2004 | Dinsdale et al. |
| 6,730,091 | B1 * | 5/2004 | Pfefferle et al. ............. 606/70 |
| 6,821,278 | B2 * | 11/2004 | Frigg et al. .................... 606/69 |
| 6,960,213 | B2 | 11/2005 | Chervitz et al. |
| 2001/0037112 | A1 | 11/2001 | Brace et al. |
| 2001/0047174 | A1 | 11/2001 | Donno et al. |
| 2002/0045901 | A1 | 4/2002 | Wagner et al. |
| 2002/0058940 | A1 | 5/2002 | Frigg et al. |
| 2002/0143338 | A1 | 10/2002 | Orbay et al. |
| 2003/0018335 | A1 | 1/2003 | Michelson |
| 2004/0044345 | A1 | 3/2004 | DeMoss et al. |
| 2004/0073218 | A1 | 4/2004 | Dahners |
| 2004/0087954 | A1 | 5/2004 | Allen et al. |
| 2005/0107796 | A1 | 5/2005 | Gerlach et al. |

FOREIGN PATENT DOCUMENTS

| | | |
|---|---|---|
| EP | 0 355 035 B1 | 2/1990 |
| EP | 0 486 762 B1 | 5/1995 |
| EP | 0 468 192 B1 | 9/1996 |
| EP | 0 760 632 B1 | 3/1997 |
| EP | 1169971 | 1/2002 |
| WO | WO 01/19267 A1 | 3/2001 |
| WO | WO 01/91660 | 12/2001 |
| WO | WO 02/058574 | 8/2002 |
| WO | WO 02/096309 A1 | 12/2002 |
| WO | WO 05/032386 A1 | 4/2005 |

OTHER PUBLICATIONS

Bolhofner, et al., "The Results of Open Reduction and Internal Fixation of Distal Femur Fractures Using a Biologic (Indirect) Reduction Technique," *Journal of Orthopaedic Trauma*, 10(6):371-377 (1996).

Farouk, et al., "Minimally invasive plate osteosynthesis and vascularity: preliminary results of a cadaver injection study," *Injury*, 28(Supp. 1):S-A7-S-A12 (1997).

Farouk, et al., "Minimally Invasive Plate Osteosynthesis: Does Percutaneous Plating Disrupt Femoral Blood Supply Less Than the Traditional Technique?", *Journal of Orthopaedic Trauma*, 13(6):401-406 (1999).

Frigg, et al., "The development of the distal femur Less Invasive Stabilization System (LISS)," *Injury, Int. J. Care Injured*, 32(S-C24-31 (2001).

Gerber, et al., "Biological internal fixation of fractures," *Arch. Orthop. Trauma Surg.*, 109:295-303 (1990).

Karnezis, et al., "'Biological' internal fixation of long bone fractures: a biomechanical study of a 'noncontact' plate system," *Injury*, 29(9):689-695 (1998).

Koval, et al., "Distal Femoral Fixation : A Biomechanical Comparison of the Standard Condylar Buttress Plate, a Locked Buttress Plate, and the 95-Degree Blade Plate," Journal of Orthopaedic Trauma, 11(7):521-524 (1997).

Krettek, et al., "Minimally invasive percutaneous plate osteosynthesis (MIPPO) using the DCS in proximal and distal femoral fractures," *Injury*, 28(Supp. 1):S-A20-S-A30 (1997).

Krettek, et al., "Intraoperative control of axes, rotation and length in femoral and tibial fractures," *Injury*, 29(Supp. 3):S-C-29-S-C39 (1998).

Miclau, et al., "A Mechanical comparison of the Dynamic Compression Plate, Limited Contact-Dynamic Compression Plate, and Point Contact Fixator," *Journal of Orthopaedic Trauma*, 9(1):17-22 (1995).

Rüedi, et al., "New Techniques in Indirect Reduction of Long Bone Fractures," *Clinical Orthopaedics and Related Research*, No. 347:27-34 (1998).

Schavan, et al., "LISS—The Less Invasive Stabilization System for Metaphyseal Fractures of Femur and Tibia," *OTA 98 Posters* (1998).

Marti, et al., "Biomechanical Evalutaion of the Less Invasive Stabilization System for the Internal Fixation of Distal Femur Fractures," *Journal of Orthopaedic Trauma*, 15(7):482-487, 2001.

* cited by examiner

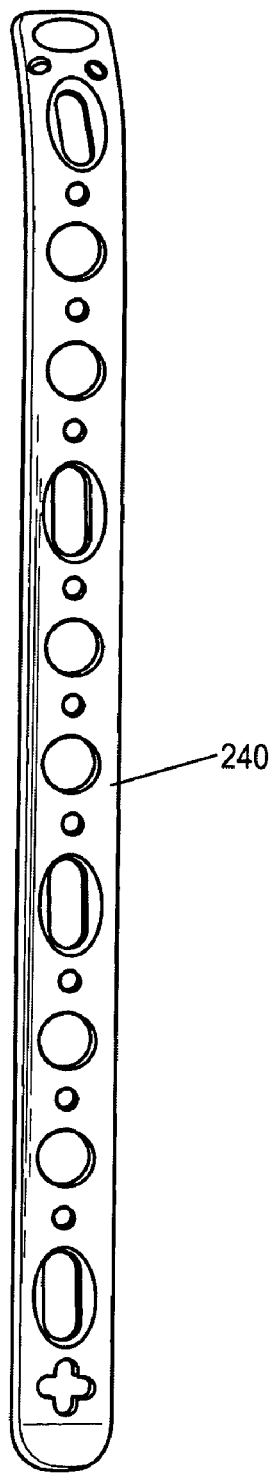
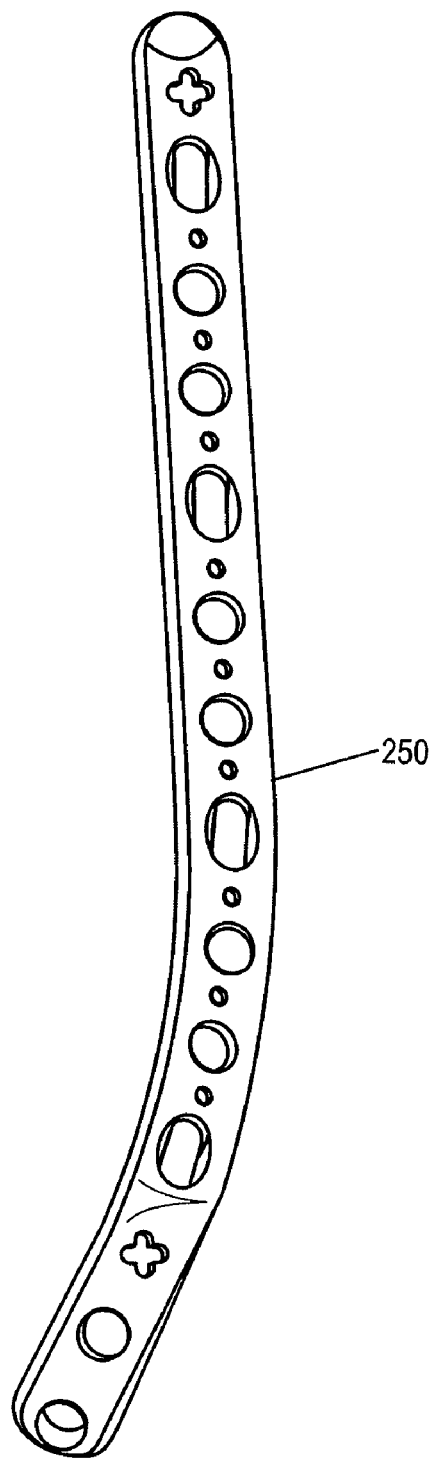
*Fig. 24*  *Fig. 25*

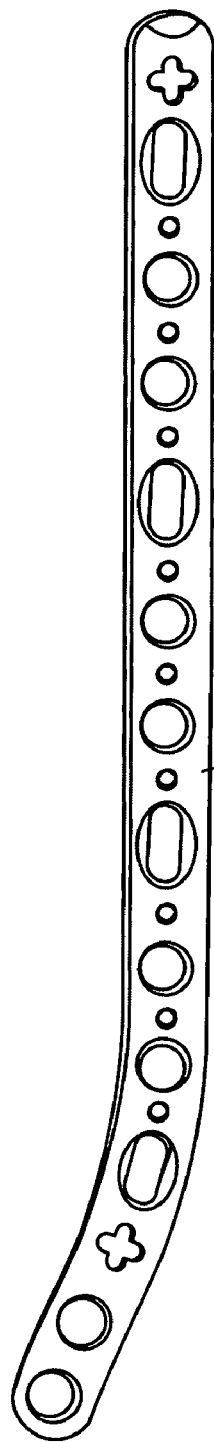
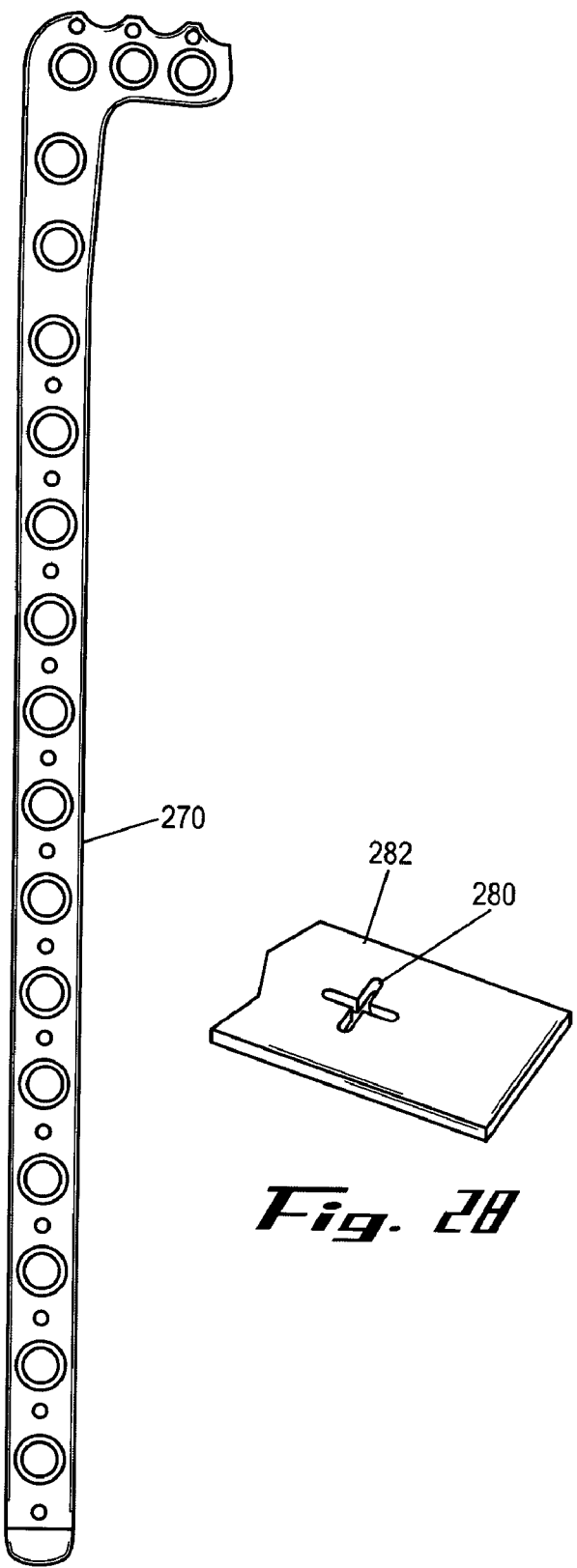
Fig. 26  Fig. 27  Fig. 28

US 7,179,260 B2

BONE PLATES AND BONE PLATE ASSEMBLIES

FIELD OF THE INVENTION

The invention relates generally to apparatuses for fixation of parts of a fractured bone, and, more particularly, to bone plates and bone plate assemblies, including bone plates and screws, for stabilization and compression of parts of a fractured bone.

BACKGROUND OF THE INVENTION

Bone fractures lead to complex tissue injuries involving both the bone and the surrounding soft tissue. Treated in a conservative way, fractures often result in malalignment or non-unions and may also lead to stiffness of adjacent joints. To reduce the occurrence of these problems, open reduction and internal fixation of the bone can be carried out. Anatomical reduction and stable internal fixation with plates and screws are very successful in treating bone fractures.

Good bone healing can also result from relative stability, where the clinical outcome is often dependent on obtaining correct length, axis, and rotation of the fractured bone rather than on precise anatomical reduction and absolute stability. To achieve this, while at the same time minimizing the amount of additional soft tissue trauma, treatment of multi-fragmented metaphyseal and diaphyseal fractures with plates and screws was developed.

An existing solution is plate and screw systems where the screws are locked in the plate. The plate and screws form one stable system and the stability of the fracture is dependent upon the stiffness of the construct. No compression of the plate onto the bone is required, which reduces the risk of primary loss of reduction and preserves bone blood supply. Locking the screw into the plate to ensure angular, as well as axial, stability eliminates the possibility for the screw to toggle, slide, or be dislodged and thereby strongly reduces the risk of postoperative loss of reduction. As the relationship between the locking screws and the plate is fixed, locking screws provide a high resistance to shear or torsional forces, but locking screws have a limited capability to compress bone fragments.

Because of this shortcoming, many surgeons began expressing the desire to have plate and screw systems (or bone plate assemblies) where the surgeon can choose intra-operatively whether to use the bone plate with compression screws (also referred to as cortical or cancellous screws), locking screws, or with a combination of both. This led to the development of a combination slot, a compression slot combined with a partially threaded opening, that could receive either a compression screw or a locking screw.

Bone plate assemblies that combine compression screws and locking screws are ideal in certain clinical situations. Bone plates with combination slots, including partially threaded openings, are well known to those skilled in the art. The partially threaded portions allow either locking or compression screws to be used. Because the slots are only partially threaded, the locking screws may not be able to maintain the fixed angular relationship between the screws and plate under physiological loads. Specifically, the locking screws within the plate are only partially captured and thus only partially surrounded by threads. Under high stress and loading conditions, the slot may distort and allow the fixed angular relationship between the locking screw and plate to change. This can result in loss of fixation or loss of established intraoperative plate orientation. Additionally, because of the slot geometry, translation of the plate with compressions screws may be limited to a single direction, which may be disadvantageous in reduction and manipulation of fragments.

Accordingly, there is a need for improved bone plates that may be used with both compression and locking screws for improved stabilization and compression of parts of a fractured bone.

SUMMARY OF THE INVENTION

The present invention provides bone plates and bone plate assemblies for stabilization and compression of parts of a fractured bone. According to an exemplary embodiment of the present invention, a bone plate includes an upper surface, a bone contacting surface, and at least one hole extending through the upper surface and the bone contacting surface that may interchangeably receive a locking screw and a compression screw, wherein each hole includes a thread that makes a complete revolution around the hole.

According to certain exemplary embodiments, each hole may include a top portion extending from the upper surface and a threaded bottom portion extending from the top portion to the bone contacting surface. The top portion of the hole may extend from the upper surface of the bone plate at a first angle relative to the plane of the upper surface. The top portion of the hole may include a ramp extending from the upper surface at a first angle relative to the plane of the upper surface and a concave recessed portion that is generally spherical. The first angle may be fifty-two degrees in either instance. The bottom portion of the hole may be generally cylindrical or tapered with an included angle of less than about thirty degrees. The included angle may be about twenty degrees. Each hole is configured to engage a head of a compression screw and provide compression of fractured bone fragments. Using a compression screw, fine adjustment of a fracture of up to two millimeters in more than one direction is possible. Each hole is configured to threadably engage a head of a locking screw and fix the locking screw with respect to the bone plate.

In another exemplary embodiment, a bone plate includes an upper surface, a bone contacting surface, and at least one hole extending through the upper surface and the bone contacting surface that may interchangeably receive a locking screw and a compression screw, wherein each hole includes (a) a top portion extending from the upper surface and (b) a bottom portion extending from the top portion to the bone contacting surface, wherein the bottom portion is threaded to receive threads of a head of a locking screw and the bottom portion includes at least one thread that makes a complete revolution around the hole. In certain embodiments, the top portion extends from the upper surface at a first angle relative to the plane of the upper surface and the bottom portion is tapered with an included angle of less than about thirty degrees. The first angle may be about fifty-two degrees and the included angle may be about twenty degrees. In certain embodiments, the top portion includes a ramp extending from the upper surface at a first angle relative to the plane of the upper surface and a concave recessed portion that is generally spherical and the bottom portion is generally cylindrical.

In another exemplary embodiment according to this invention, a bone plate assembly includes a bone plate, at least one locking screw, and at least one compression screw. The bone plate includes an upper surface, a bone contacting surface, and at least one hole extending through the upper surface and the bone contacting surface that may interchangeably receive a locking screw and a compression screw, wherein each hole includes a thread that makes a complete revolution around the hole.

In certain exemplary embodiments of a bone plate assembly, a hole is configured to engage a head of the compression screw and provide compression of fractured bone fragments. Each hole may be configured to engage a head of the compression screw such that fine adjustment of a fracture of up to two millimeters in more than one direction is possible and to threadably engage a head of a locking screw and fix the locking screw with respect to the bone plate.

In certain exemplary embodiments of a bone plate assembly, a head of the locking screw may include threads that engage threads in the hole. Both the head of the locking screw and the hole may be tapered. The head of the locking screw and at least a portion of the hole may be tapered at an included angle of less than about thirty degrees. The locking screw may include a head with triple lead threads and a single lead threaded shaft such that all threads of the locking screw are of a constant pitch. In certain embodiments, the lead of threads of the locking screw is not continuous between the threads of the head and the threads of the shaft of the locking screw. Each hole of the bone plate may include a top portion extending from the upper surface and a threaded bottom portion extending from the top portion to the bone contacting surface.

Certain exemplary embodiments of this invention also include methods of reducing a fracture.

BRIEF DESCRIPTION OF THE DRAWINGS

FIGS. 10–27 are perspective views of various exemplary bone plate configurations according to various embodiments of the present invention, without threads of any holes or other openings shown.

FIG. 28 shows a provisional fixation slot according to one embodiment of the present invention.

DETAILED DESCRIPTION OF THE INVENTION

The present invention provides bone plates and bone plate assemblies for stabilization and compression of parts of a fractured bone. According to certain exemplary embodiments of this invention, a bone plate includes an upper surface, a bone contacting surface, and at least one hole extending through the upper surface and the bone contacting surface that may interchangeably receive a locking screw and a compression screw. The bone plate may include additional openings that receive only compression screws or only locking screws.

A threaded head of an exemplary locking screw for use in accordance with this invention is received by threads in a corresponding hole such that the threads of the hole completely surround the threads of the head of the locking screw. This relationship between the head of the locking screw and the threads of the hole contributes to maintaining fixation of the bone plate and strengthening the plate and screw combination. As noted, a compression screw may also be received within the hole of the bone plate. As the compression screw is fully inserted within a bone, the head of the compression screw comes into contact with and rides along a top portion of the hole, allowing for fine adjustment of the position of the bone plate in more than one direction.

Figure 1A:
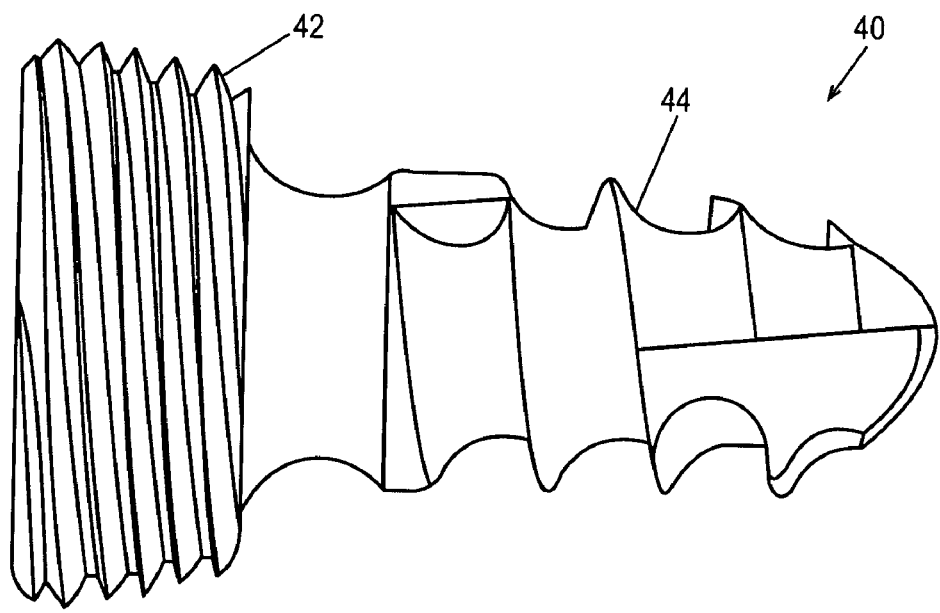
FIG. 1A shows a side view of an exemplary locking screw according to one embodiment of the present invention.
Figure 1B:
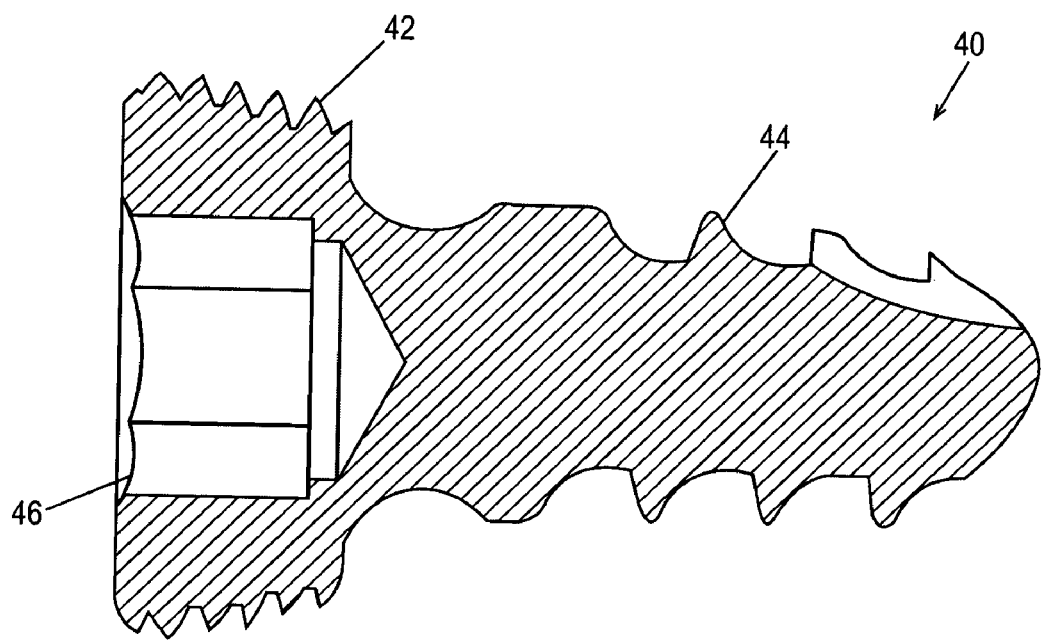
FIG. 1B shows a cross-sectional view of the locking screw of FIG. 1A.

FIGS. 1A and 1B show an exemplary locking screw for use according to one embodiment of the present invention. A locking screw 40 includes a threaded head 42 and a threaded shaft 44. Locking screw 40 may be a 3.5 mm, 4.5 mm, 6.5 mm, or other size locking screw, which is understood by those skilled in the art. In the exemplary embodiment shown in FIGS. 1A and 1B, the lead between the threads of head 42 and the threads of shaft 44 is broken. The threads in shaft 44 of locking screw 40 are single lead and the threads in head 42 are triple lead, providing locking screw 40 with same pitch throughout. It is preferable for certain embodiments of locking screws according to this invention to have a constant pitch. In an exemplary 3.5 mm locking screw, the pitch is 1.25 mm and the angle of the thread form is about 45 to about 60 degrees. In an exemplary 4.5 mm locking screw, the pitch is 1.75 mm and the angle of the thread form is about 60 degrees. Locking screw 40 also includes an internal hex head 46, as shown in FIG. 1B, that is used when tightening locking screw 40 into a bone plate and/or bone.

FIGS. 2A–2E show different views of a portion of a bone plate according to an embodiment of the present invention. Such bone plates generally include one or more holes or other openings, such as in the exemplary bone plates shown in FIGS. 10–27, which are briefly described below. However, for ease of illustration and for purposes of describing an exemplary embodiment of the present invention, only a portion of bone plate 50 is shown in FIGS. 2A–2E.

Figure 2A:
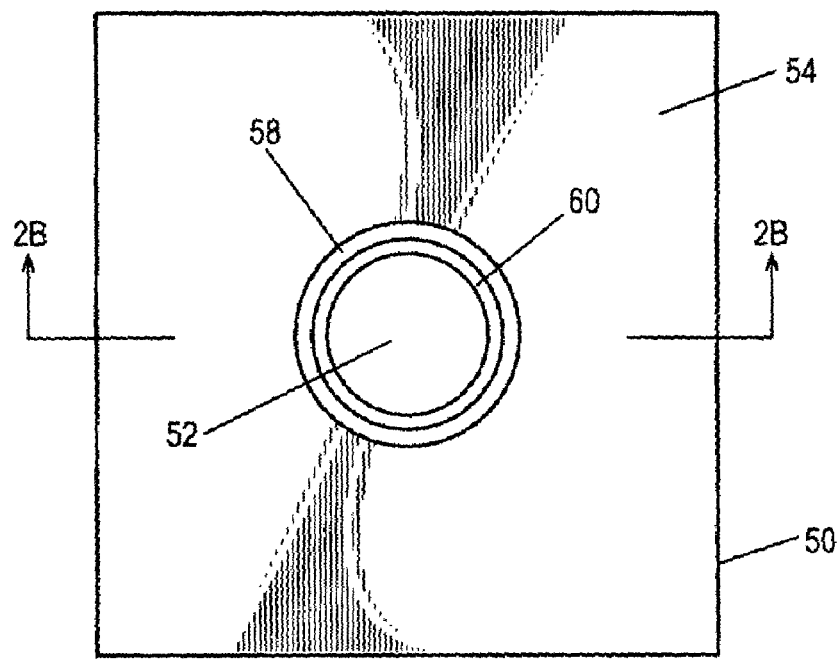
FIG. 2A shows a top view of a portion of a bone plate, including a hole without the threads of the hole shown, according to one embodiment of the present invention.
Figure 2B:
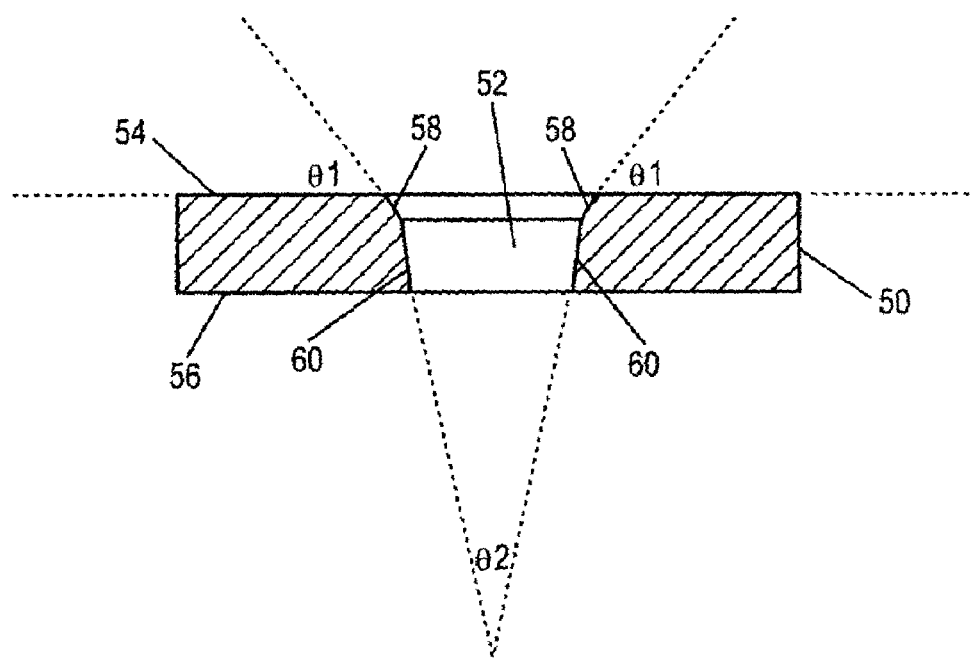
FIG. 2B shows a cross-sectional view of the portion of the bone plate shown in FIG. 2A as viewed along cross-section lines 2B—2B of FIG. 2A.
Figure 2C:
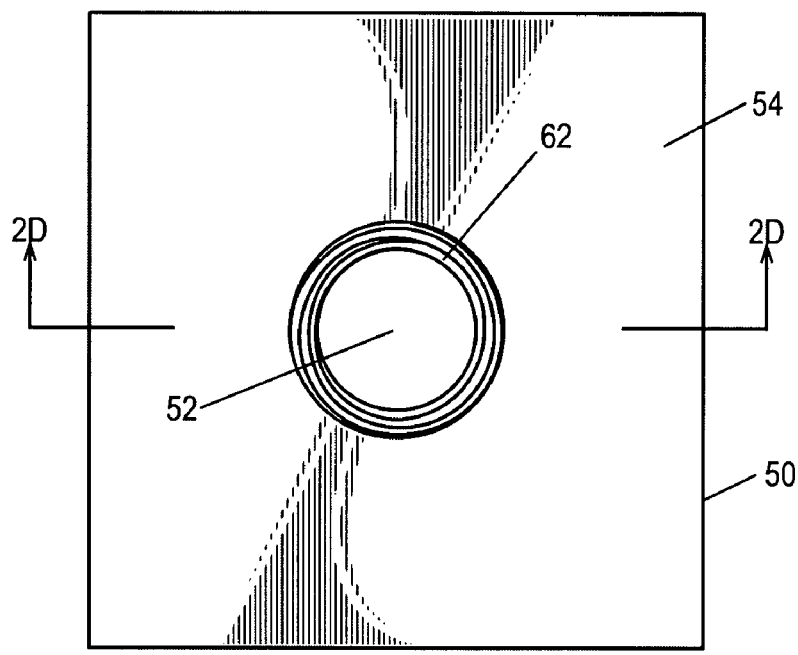
FIG. 2C shows a top view of the portion of the bone plate shown in FIGS. 2A and 2B, with the threads of the hole shown.
Figure 2D:
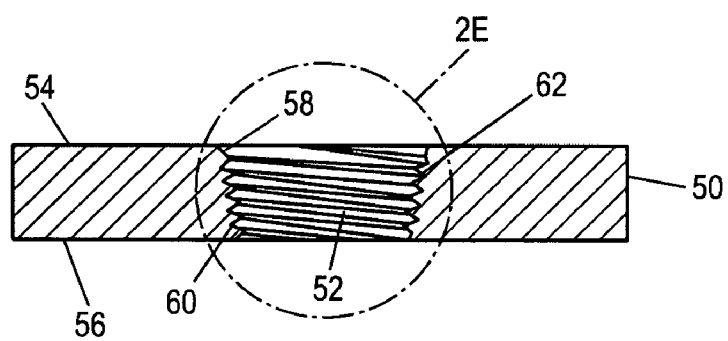
FIG. 2D shows a cross-sectional view of the portion of the bone plate shown in FIGS. 2A–2C as viewed along cross-section lines 2D—2D of FIG. 2C.
Figure 2E:
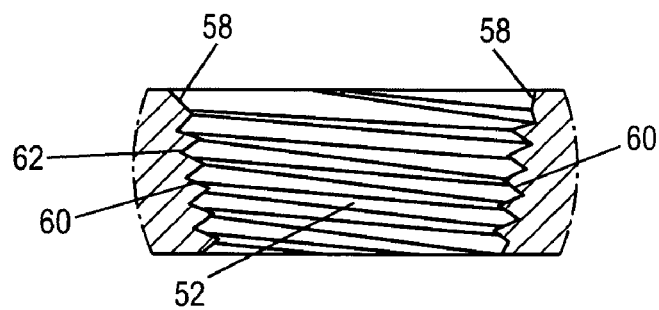
FIG. 2E shows a detailed view of the hole of the portion of the bone plate shown in FIGS. 2A–2D.

The particular bone plate 50 shown in these drawings includes a hole 52 extending through an upper surface 54 and a bone contacting surface 56 of bone plate 50. FIGS. 2A and 2B show hole 52 without its threads to help illustrate certain aspects of this embodiment of the invention, while FIGS. 2C–2E show hole 52 with its threads. It should be understood that the geometry of hole 52 is the same throughout these drawings, although the geometry of hole 52 is not as clearly visible in the drawings that show the threads of hole 52. As seen most clearly in FIG. 2B, hole 52 includes a top portion 58 extending downward from upper surface 54. Top portion 58 extends from upper surface 54 at an angle of θ1 relative to the plane of top surface 54, as shown in FIG. 2B. In an exemplary embodiment, angle θ1 is about fifty-two degrees.

A bottom portion 60 of hole 52 extends from the end of top portion 58 through bone contacting surface 56 of bone plate 50. Bottom portion 60 includes threads 62, as shown in FIGS. 2C–2E. Some of threads 62 may extend into top portion 58 depending on the particular embodiment, but top portion 58 is not completely threaded.

In the exemplary embodiment shown in FIGS. 2A–2E, bottom portion 60 is tapered. The included angle, θ2 shown in FIG. 2B, of the taper of bottom portion 60 may be less than about thirty degrees, including zero degrees (i.e., no taper at all). The larger the included angle, the larger hole 52 in bone plate 50 must be, which begins to compromise the strength of the plate if the included angle is much larger than about thirty degrees. In an exemplary embodiment, θ2 is about twenty degrees.

Figure 3:
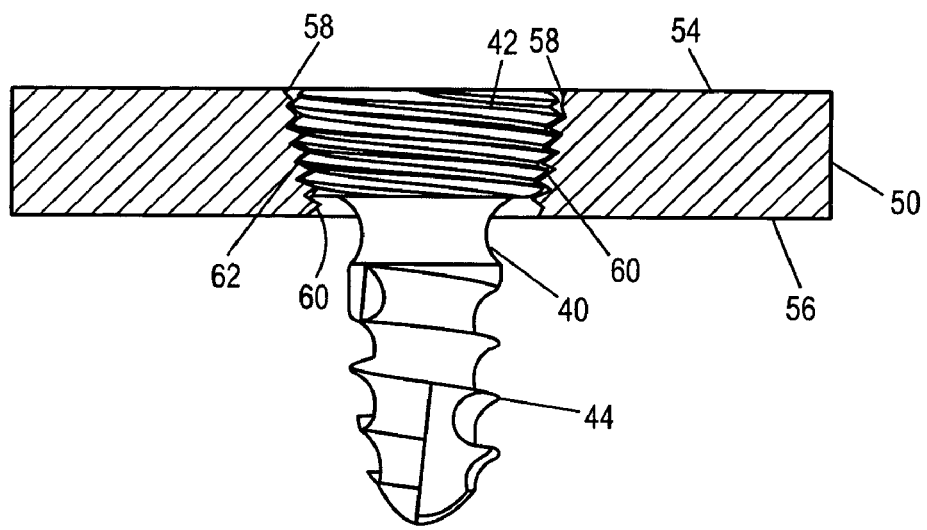
FIG. 3 shows a side view of the locking screw of FIGS. 1A and 1B threaded into the portion of the bone plate shown in FIGS. 2A–2E.

FIG. 3 shows a side view of locking screw 40 threaded into hole 52 of bone plate 50. Head 42 of locking screw 40 is received by threads 62 of bone plate 50. Threads 62 completely surround the threads of head 42, and the top of head 42 is received completely within hole 52 such that head 42 of locking screw 40 sits flush with upper surface 54 of bone plate 50. Shaft 44 of locking screw 40 is threaded into a bone (not shown). Head 42 of locking screw 40 should be tapered such that it properly mates with threads 62 of hole 52 of bone plate 50. Furthermore, a threaded portion of a head of a locking screw for use with certain embodiments of this invention should have a taper generally corresponding to the taper, if any, of the threads of the hole of the bone plate.

Figure 4:
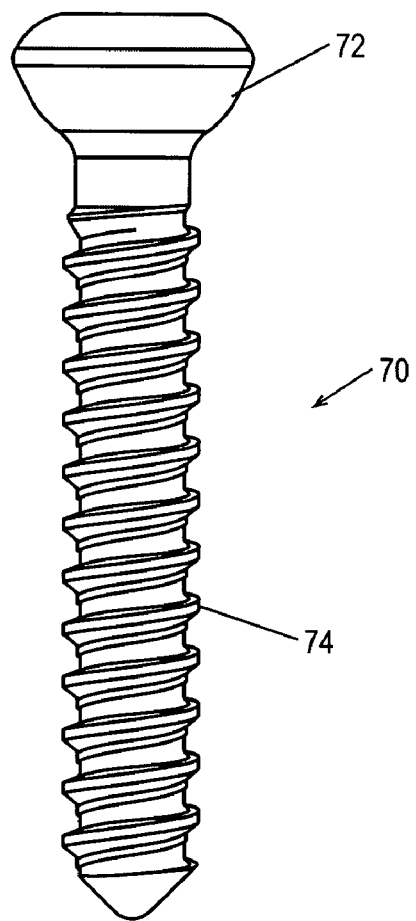
FIG. 4 shows a side view of an exemplary compression screw for use according to one embodiment of the present invention.
Figure 5:
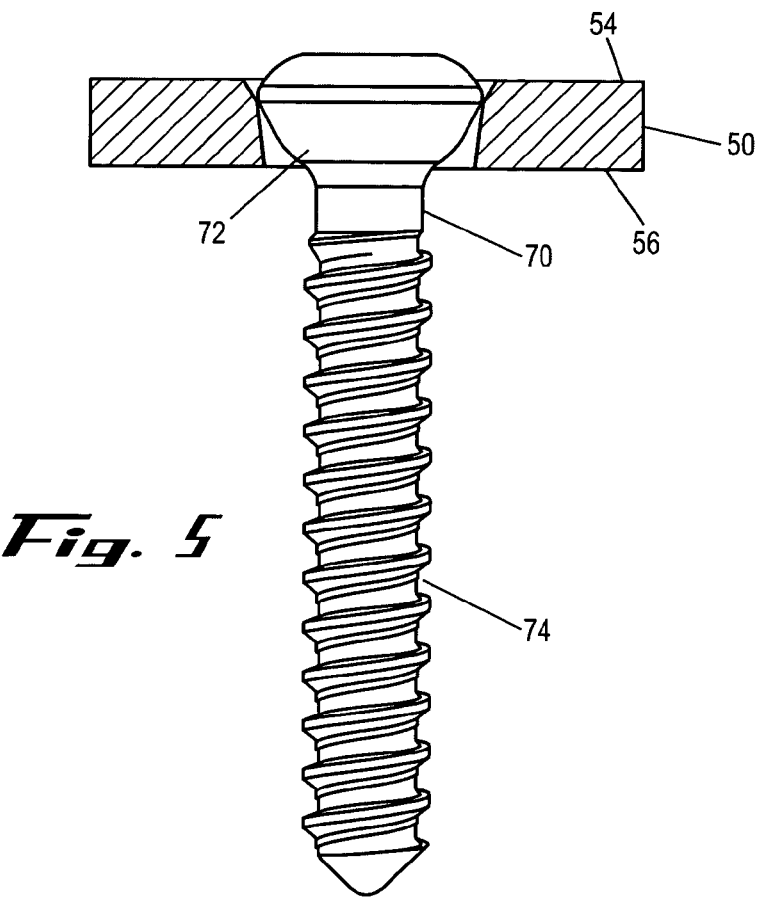
FIG. 5 shows a side view of the compression screw of FIG. 4 inserted into the portion of the bone plate shown in FIGS. 2A–2E.

FIG. 4 shows a side view of an exemplary compression screw for use according to an embodiment of the present invention. A compression screw 70 includes a head 72 and a threaded shaft 74. FIG. 5 shows compression screw 70 inserted within hole 52 of bone plate 50. As shown in FIG. 5, head 72 of compression screw 70 rides along top portion 58 of bone plate 50. As shaft 74 is threaded into a bone (not shown), compression screw 70 may pull or push bone plate 50 in a particular direction as head 72 of compression screw 70 comes into contact with and rides along top portion 58 of hole 52 of bone plate 50. The angle θ1, shown in FIG. 2B, at top portion 58 of hole 52 is significant for compression of a fracture and is necessary to help shift the bone plate in the desired direction. If top portion 58 were to extend straight down from upper surface 54 of bone plate 50, compression would be less successful. Compression screw 70 may move bone plate 50 in more than one direction as compression screw 70 is fully inserted within hole 52. In an exemplary embodiment, fine adjustment of fractures up to about two millimeters in several directions is possible.

Figure 6A:
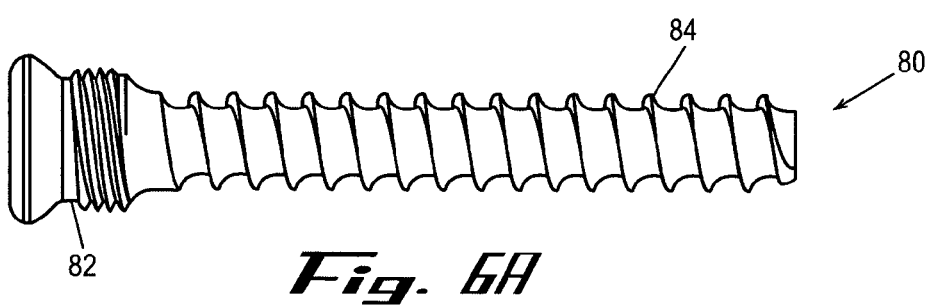
FIG. 6A shows a side view of an exemplary locking screw according to an embodiment of the present invention.
Figure 6B:
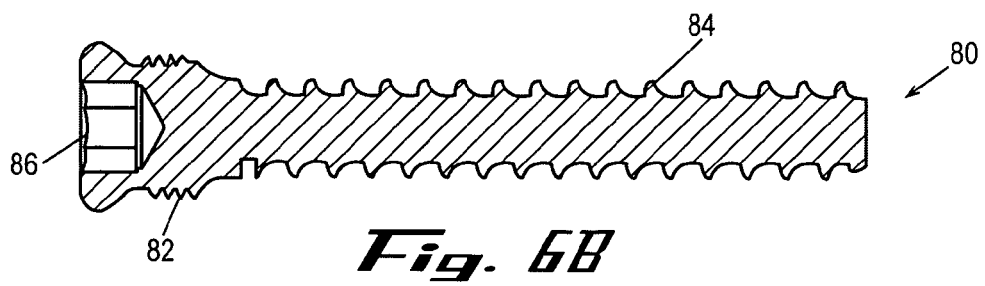
FIG. 6B shows a cross-sectional view of the locking screw of FIG. 6A.

FIGS. 6A and 6B show another exemplary locking screw for use according to an embodiment of the present invention. A locking screw 80 includes a head 82 and a threaded shaft 84. Similar to locking screw 40 shown in FIGS. 1A and 1B, locking screw 80 may be a 3.5 mm, 4.5 mm, 6.5 mm, or other size locking screw, which is understood by those skilled in the art, and the lead between the threads of head 82 and the threads of shaft 84 is broken. The threads in shaft 84 of locking screw 80 are single lead and the threads in head 82 are triple lead, providing locking screw 80 with the same pitch throughout. The pitches and angles of thread form for exemplary 3.5 and 4.5 mm locking screws 80 are generally similar to those described above with reference to locking screw 40.

Locking screw 80 also includes an internal hex head 86, as shown in FIG. 6B, that is used when tightening locking screw 80 into a bone plate and/or bone. As may be seen from FIGS. 1A, 1B, 6A, and 6B, only a portion of head 82 of locking screw 80 is threaded, whereas the entire head 42 of locking screw 40 is threaded. Additionally, the threaded portion of head 82 of locking screw 80 is not tapered, while head 42 of locking screw 40 is tapered. These differences are because locking screw 40 is designed to mate with hole 52 of bone plate 50, while locking screw 80 is designed to mate with a hole 92 of a bone plate 90, as further described below.

Figure 7A:
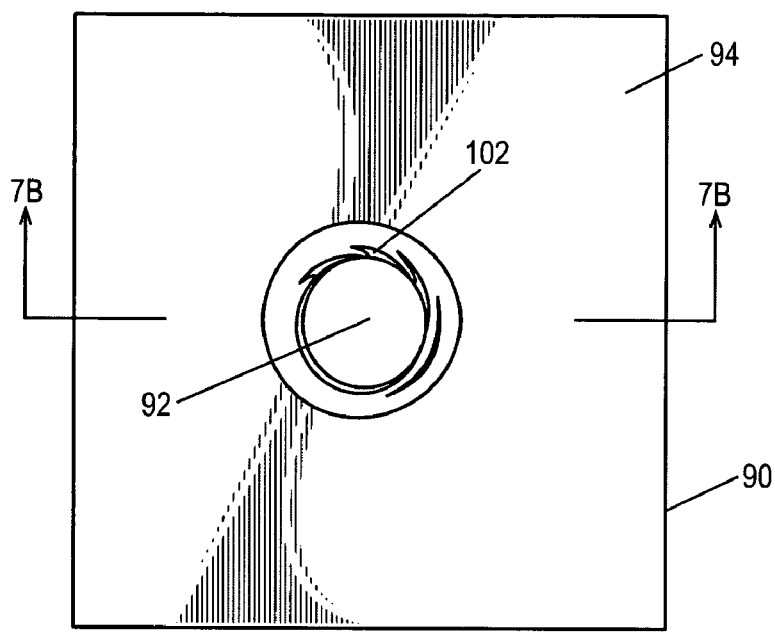
FIG. 7A shows a top view of a portion of a bone plate according to an embodiment of the present invention.
Figure 7B:
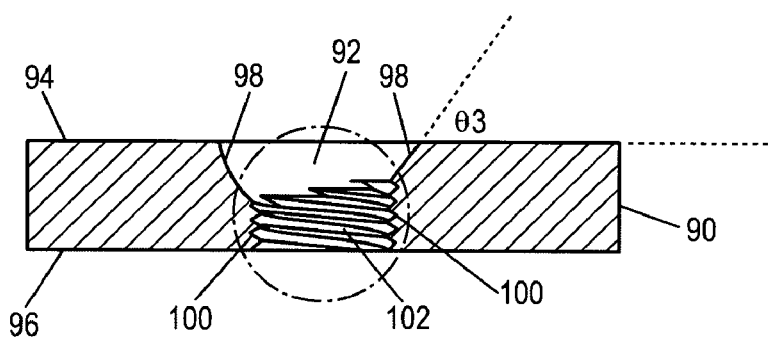
FIG. 7B shows a cross-sectional view of the portion of the bone plate shown in FIG. 7A as viewed along cross-section lines 7B—7B of FIG. 7A.
Figure 7C:
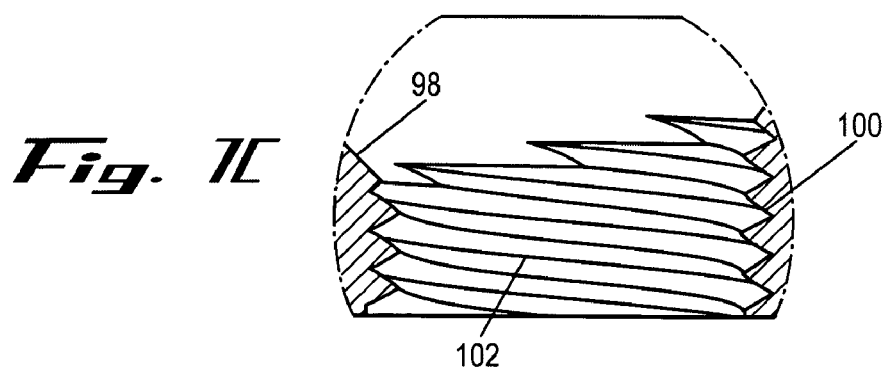
FIG. 7C shows a detailed view of the hole of the portion of the bone plate shown in FIGS. 7A and 7B.

FIGS. 7A–7C show different views of a portion of a bone plate according to an embodiment of the present invention. As noted above, bone plates generally include one or more holes or other openings, such as in the exemplary bone plates shown in FIGS. 10–27, but for ease of illustration, only a portion of bone plate 90 is shown in FIGS. 7A–7C.

Bone plate 90 includes a hole 92 extending through an upper surface 94 and a bone contacting surface 96 of bone plate 90. Hole 92 includes a top portion 98 extending downward from upper surface 94. As shown in FIG. 7B, one side of top portion 98 includes a ramp that extends from upper surface 94 at an angle of θ3 relative to the plane of top surface 94. In an exemplary embodiment, angle θ3 is about fifty-two degrees. The remainder of top portion 98 is a concave recessed portion that is generally spherical in shape, as shown in FIG. 7B.

A bottom portion 100 of hole 92 extends from the end of top portion 98 through bone contacting surface 96 of bone plate 90. Bottom portion 100 includes threads 102. Some of threads 102 may extend into top portion 98 depending on the particular embodiment, but top portion 98 generally has only the beginning of thread leads, if any threading. Bottom portion 100 is not tapered, but rather is generally cylindrical in shape. In certain embodiments, for example, bottom portion 60 of hole 52 of bone plate 50, bottom portion 100 may be tapered at an included angle of less than about thirty degrees.

Figure 8:
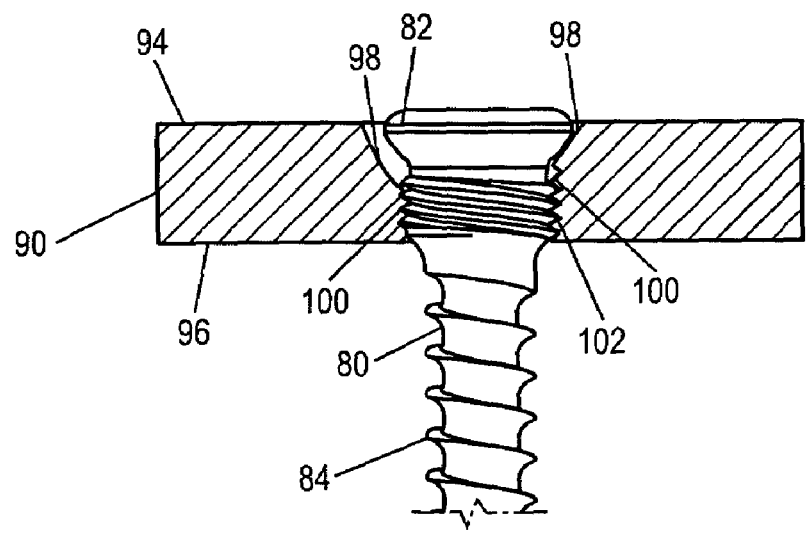
FIG. 8 shows a side view of the locking screw of FIGS. 6A and 6B threaded into the portion of the bone plate shown in FIGS. 7A–7C.

FIG. 8 shows a side view of locking screw 80 threaded into hole 92 of bone plate 90. Threads of head 92 of locking screw 90 are received by threads 102 of bone plate 90. Threads 102 completely surround the threads of head 92, and shaft 84 of locking screw 80 is threaded into bone (not shown). Head 82 of locking screw 80 is shaped such that its unthreaded portion bears against the ramp of top portion 98 of hole 92 of bone plate 90. Additionally, the threaded portion of head 82 is generally cylindrical (i.e., not tapered) so that it properly mates with threads 102 of hole 92 of bone plate 90. A threaded portion of a head of a locking screw for use with certain embodiments of this invention should be shaped to generally correspond to the shape of threaded portion of the hole of the bone plate.

Figure 9:
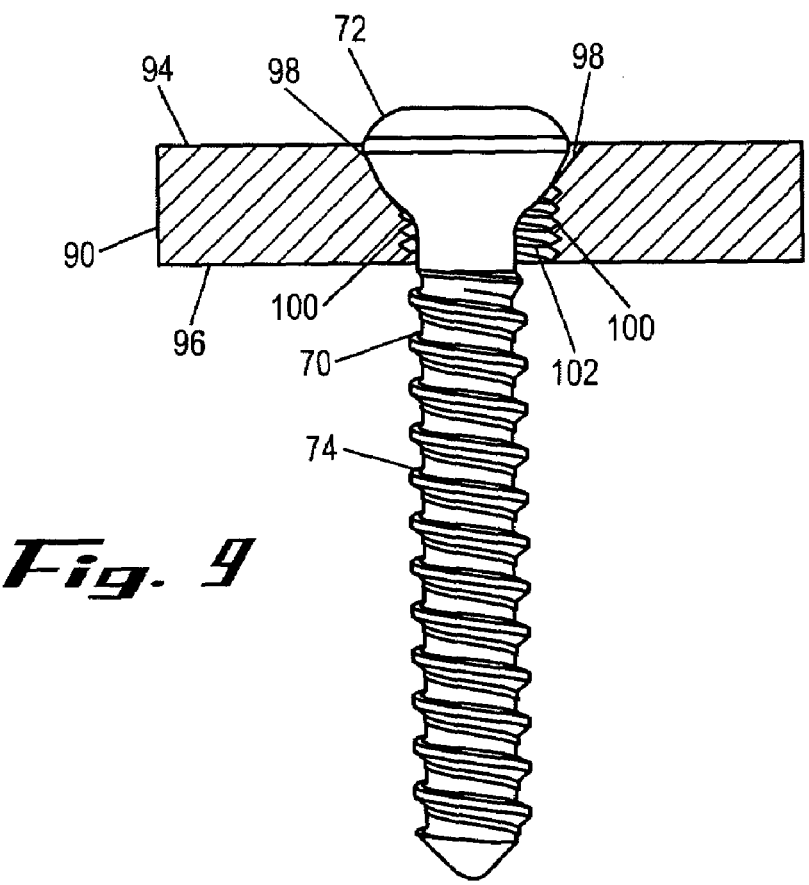
FIG. 9 shows a side view of the compression screw of FIG. 4 inserted into the portion of the bone plate shown in FIGS. 7A–7C.

FIG. 9 shows compression screw 70 inserted within hole 92 of bone plate 50. As shown in FIG. 9, head 72 of compression screw 70 sits within the concave recessed or spherical portion of top portion 98 of bone plate 90. Head 72 of compression screw 70 contacts the side of top portion 98 that includes the ramp, but head 72 does not completely abut the ramp of top portion 98. As shaft 74 is threaded into a bone (not shown), compression screw 70 may pull or push bone plate 90 in a particular direction as head 72 of compression screw 70 comes into contact with and rides along top portion 98 of hole 92 of bone plate 90, similar to that described above with reference to FIG. 5. The angle θ3, shown in FIG. 7B, at top portion 98 of hole 92 is significant for compression of a fracture and is necessary to help shift the bone plate in the desired direction. If top portion 98 were to extend straight down from upper surface 94 of bone plate 90, compression would be less successful. Compression screw 70 may move bone plate 90 in more than one direction as compression screw 70 is fully inserted within hole 92. In an exemplary embodiment, fine adjustment of fractures up to about two millimeters in several directions is possible.

In practice, a first screw is initially inserted through a bone plate and into a bone on one side of a fracture and then a second screw is inserted through the bone plate on the opposite side of the fracture. In an exemplary method according to an embodiment of the present invention, after the first screw is in place, a compression screw is inserted through a hole in the bone plate on a side of the fracture opposite the side of the first screw. The compression screw may be inserted through the hole and into the bone such that as the compression screw is fully inserted, the bone plate is drawn over to a desired position. By moving the bone plate, the tissue is being pulled together to reduce the fracture. Once the compression screw has been used to move the bone plate into the desired position, the compression screw may be removed from the bone and bone plate and a locking screw may be inserted through the hole in the bone plate and in the bone in the space formerly occupied by the compression screw. The locking screw can then be tightened to lock the plate into position. The replacement of the compression screw with the locking screw is not required, but a locking screw may provide more stability and rigid fixation than leaving the compression screw in place. In some modes of operation, a locking screw is placed directly in a locking hole without first inserting a compression screw in the hole. Certain embodiments of the invention contemplate using locking screws and compression screws in any order and in combination or not in combination with each other. As described above, certain embodiments of this invention provide for fine adjustment of fractures in more than one direction.

FIGS. 10–27 show various exemplary bone plate configurations that may include one or more holes, such as holes 52 and 92 described above, that are capable of interchangeably receiving compression screws and locking screws. Exemplary bone plates may also include other openings configured to receive only locking screws or only compression screws, which is well understood by those skilled in the art. All holes in the exemplary plates of FIGS. 10–27 include threads (not shown), while the other generally non-circular openings in these plates may or may not include threads depending on the purposes for which the opening is to be used.

Figure 10:
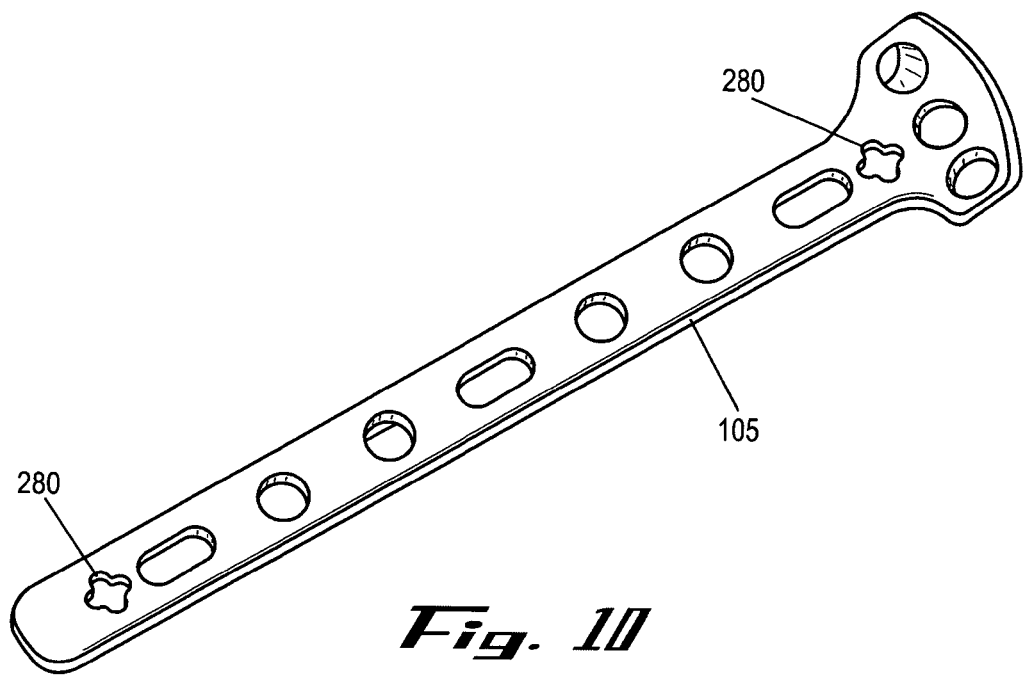
Figure 11:
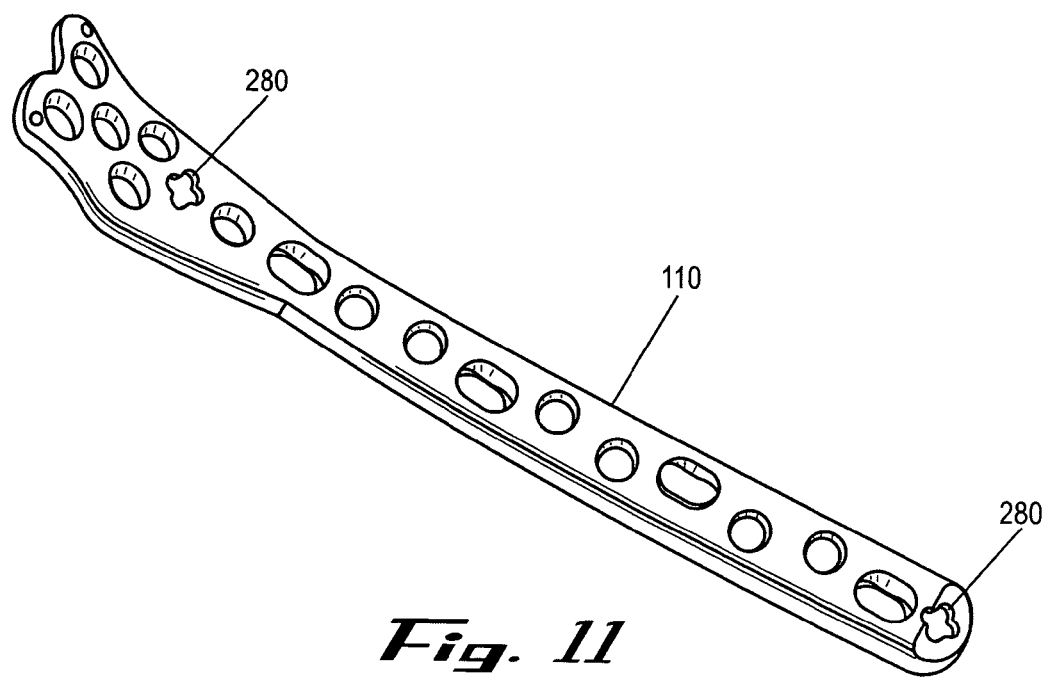
Figure 12:
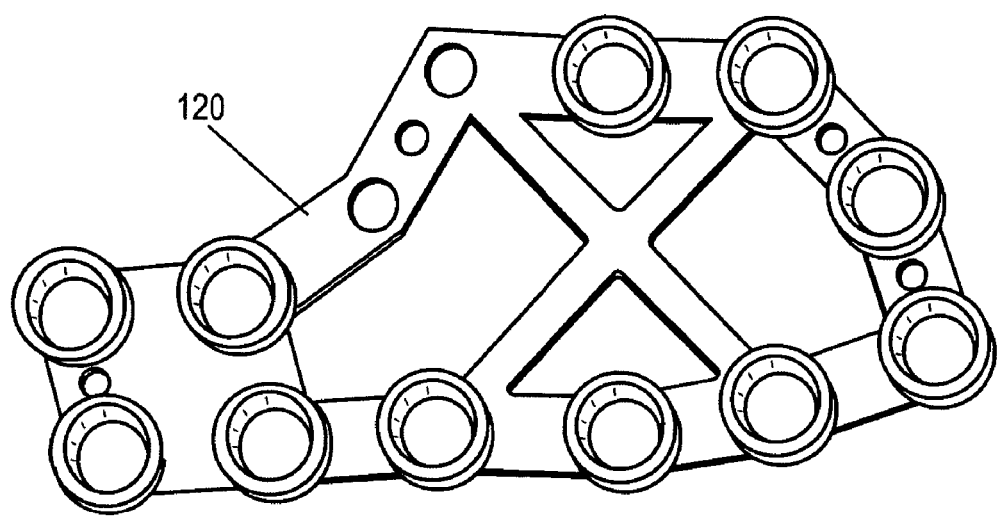
Figure 13:
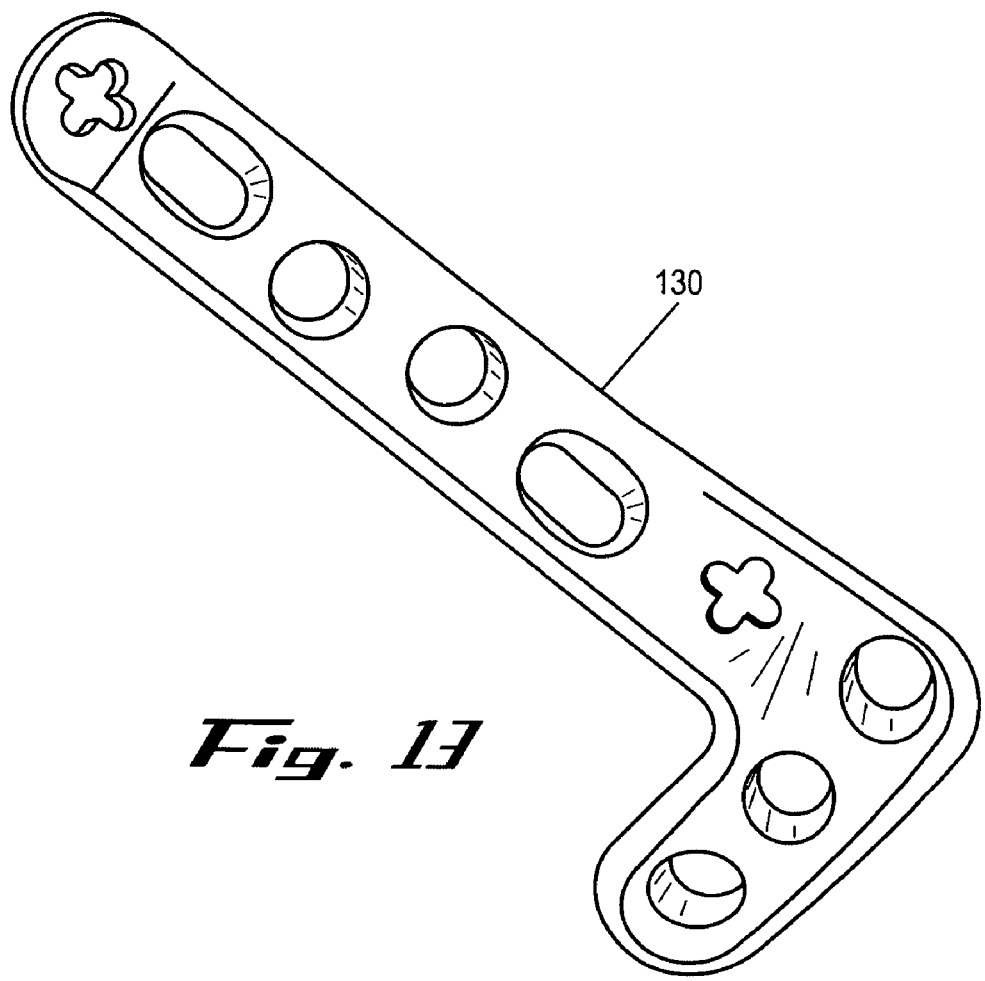
Figure 14:
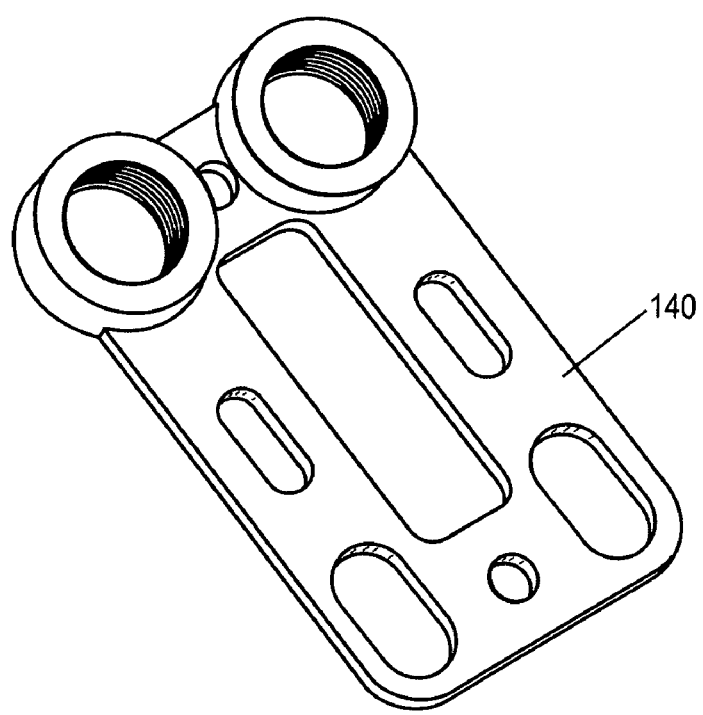
Figure 15:
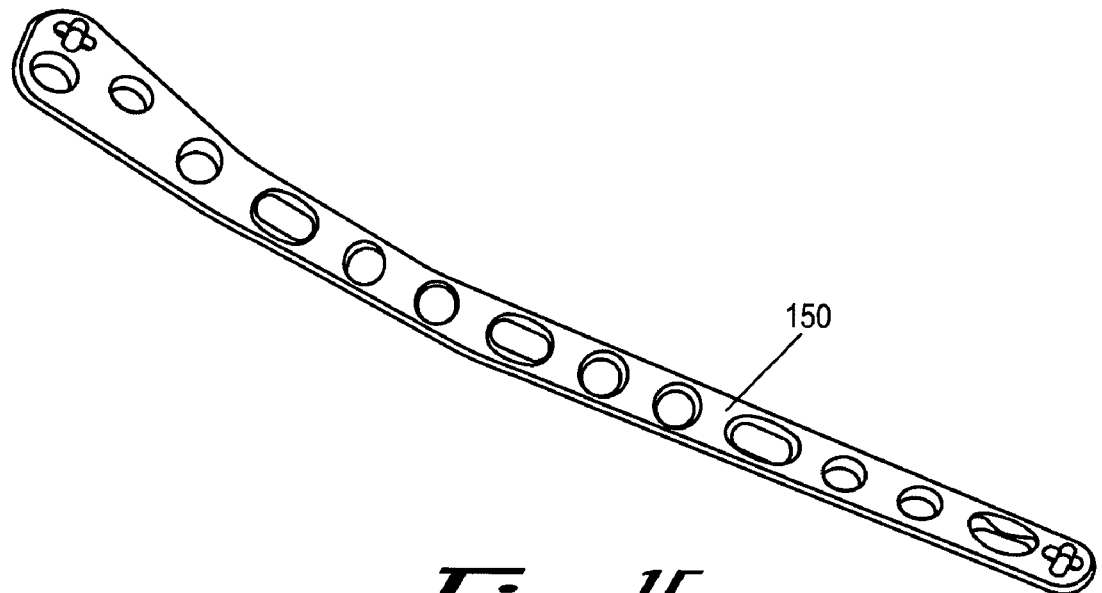
Figure 16:
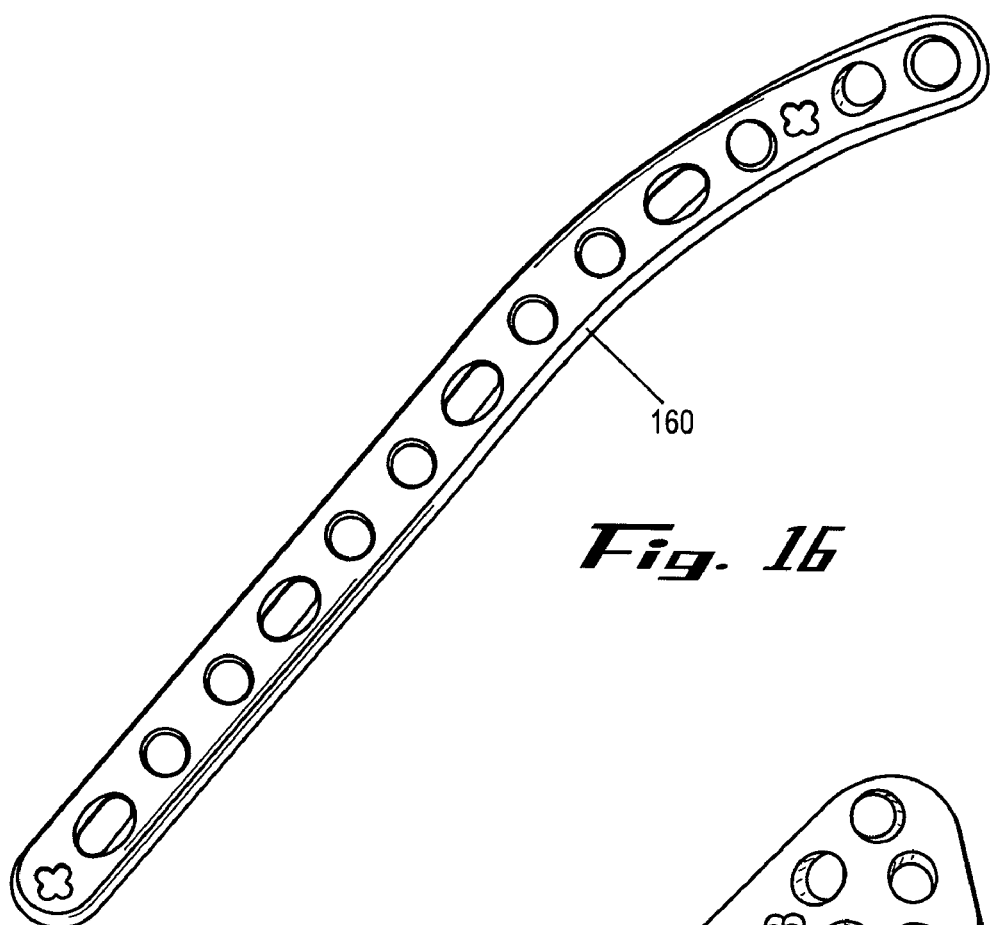
Figure 17:
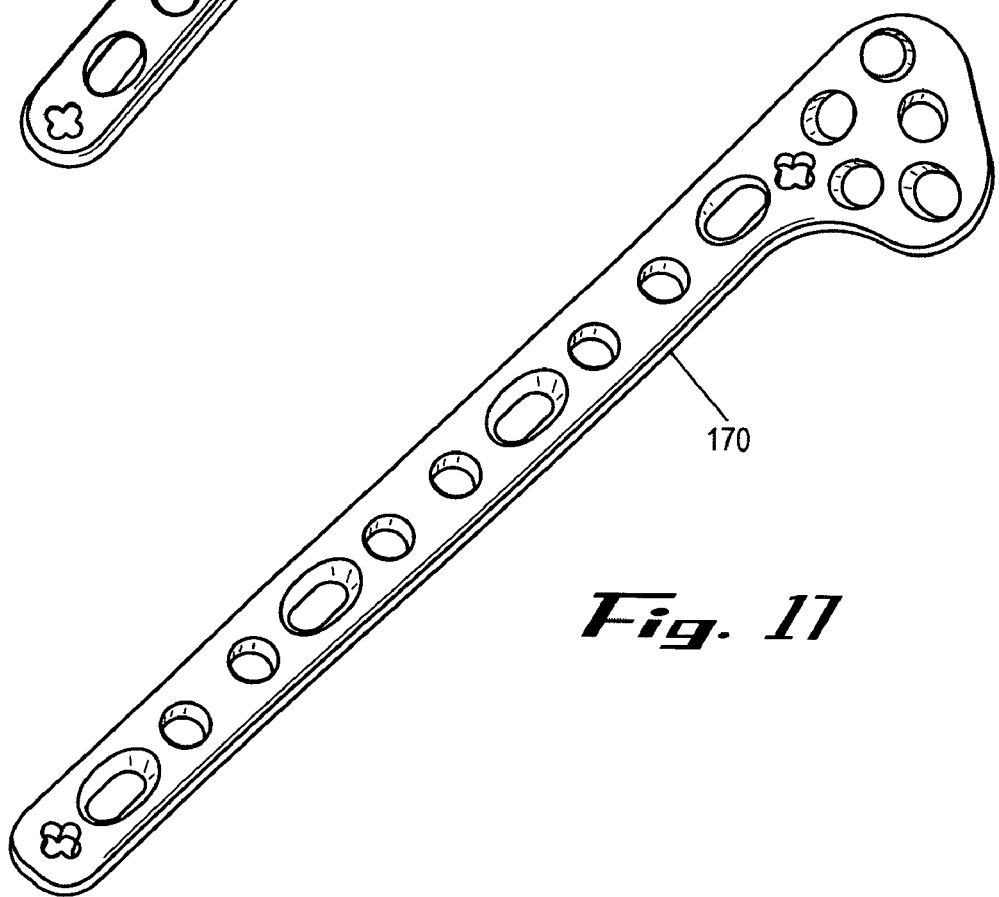
Figure 18:
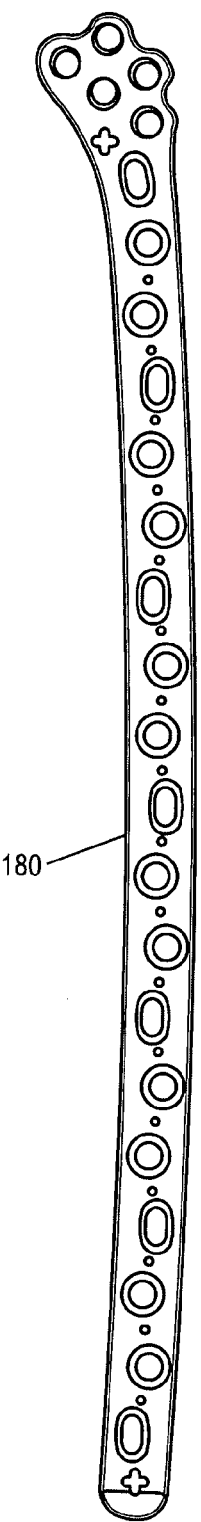

FIG. 10 shows a distal radius plate 105 that is applied on the volar aspect of the radius and used to treat fractures of the distal radius. FIG. 11 shows a distal tibia plate 110 used to treat distal tibia fractures and contoured to match the anatomy of the medial distal tibia. FIG. 12 shows a calcaneal plate 120 that is applied to the medial aspect of the calcaneus and used to treat calcaneal fractures. FIG. 13 shows a distal tibia plate 130 used to threat distal tibia fractures and contoured to match the anatomy of the lateral anterior distal tibia. FIG. 14 shows a multipurpose plate 140 used in conjunction with the calcaneal plate to fuse the talus to the calcaneus. FIG. 15 depicts a distal fibula plate 150 used to treat distal fibula fractures from the lateral side of the bone. FIG. 16 illustrates a bone plate 160 used to treat the medial distal humerus. FIG. 17 shows a proximal humerus plate 170 contoured to match the anatomy of the lateral proximal humerus. FIG. 18 illustrates a distal femur plate 180 contoured to treat fractures of the distal femur from the lateral side of the bone.

Figure 19:
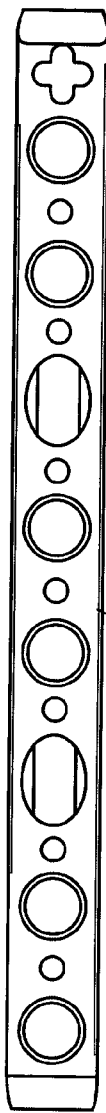
Figure 20:
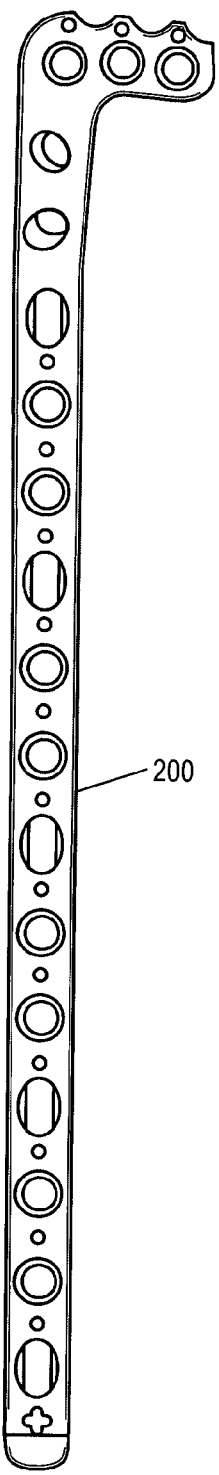
Figure 21:
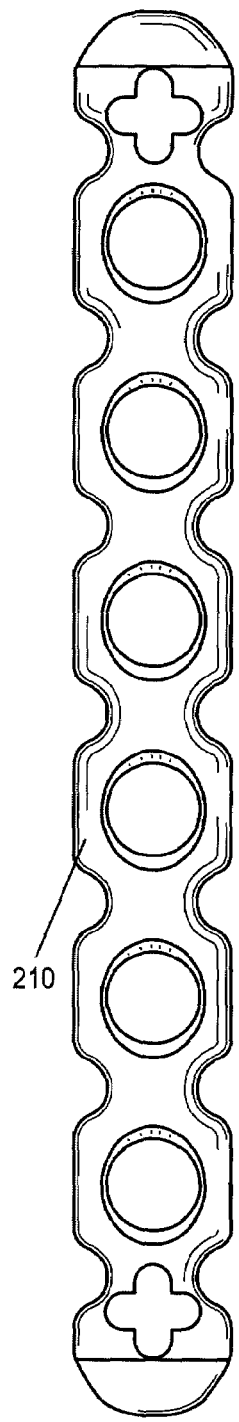
Figure 22:
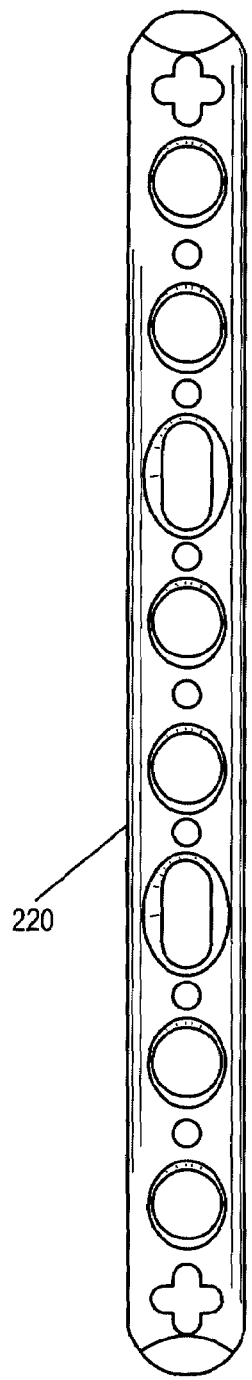
Figure 23:
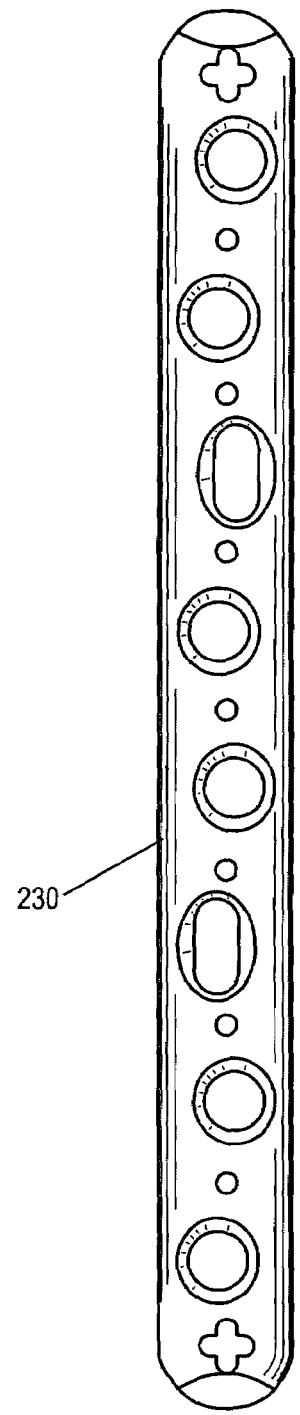

FIG. 19 shows a ⅓ tubular straight bone plate 190 used to treat small bone fractures. FIG. 20 depicts a proximal tibia plate 200 contoured to treat proximal tibia fractures from the medial side. FIG. 21 shows a reconstruction plate 210. FIG. 22 illustrates a small fragment straight plate 220, and FIG. 23 illustrates a large fragment bone plate 230. FIG. 24 illustrates an olecranon plate 240 used to treat fractures of the proximal ulna. FIG. 25 shows a distal humerus plate 250 contoured to match the anatomy of the lateral posterior distal humerus. FIG. 26 depicts a distal humerus plate 260 contoured to match the anatomy of the lateral distal humerus. FIG. 27 shows a proximal tibia plate 270 contoured to treat proximal tibia fractures from the medial side that is similar to plate 200, except that plate 270 includes only holes, such as hole 52 and hole 92, that may receive both compression and locking screws and does not include any other openings.

Shown in some of the exemplary bone plates in FIGS. 10–27 are provisional fixation slots, such as, for example, slots 280 in FIGS. 10 and 11, according to one embodiment of the present invention. FIG. 28 shows provisional fixation slot 280 in a portion of a bone plate 282. As is well known to those skilled in the art, provisional fixation pins are commonly used to provisionally affix a bone plate to the bone prior to installation of the bone plate with permanent attachment, such as bone screws. Existing provisional fixation slots typically allow only fixation of bone fragments and not any adjustability of the position of bone fragments. An embodiment of a provisional fixation slot of this invention allows articulation of bone fragments in up to six degrees of freedom to reduce the bone fracture. A bone fragment may be locked into a position and then incrementally repositioned to another temporary or permanent location. In FIG. 28, slot 280 has a cross or x shape, but the shape of slot 280 may vary according to the desired functionality and may include I, L, T, and other shape slots.

In practice, a bone plate is placed on the bone and the plate may or may not be affixed to the bone utilizing bone screws and/or provisional fixation pins. When provisional fixation is desired, a provisional fixation pin may be inserted through a provisional fixation slot and driven into the target bone fragment. The fragment may be manipulated to reduce the fracture and draw the fragment to the plate. Once the bone fragment is in a desired position, the provisional fixation pin may be tightened until the pin locks into the plate. If further movement of the bone fragment is desired, a second provisional fixation pin may be inserted in the same provisional fixation slot in a space in the slot that is not occupied by the first pin. After insertion of the second pin, the first pin may be removed and the bone fragment may be manipulated with the second pin. Once a desired position of the bone fragment is reached, the second pin is locked into the bone plate. Standard devices well known to those skilled in the art, such as screws, pins, cables, and other devices, may be used to affix the bone to the bone plate. Once the construct is sufficiently stable, any provisional fixation pins in use may be removed from the bone.

The foregoing description of exemplary embodiments of the invention has been presented only for the purposes of illustration and description and is not intended to be exhaustive or to limit the invention to the precise forms disclosed. Many modifications and variations are possible in light of the above disclosure. The embodiments were chosen and described in order to explain the principles of the invention and their practical application so as to enable others skilled in the art to make and utilize the invention and various embodiments and with various modifications as are suited to the particular use contemplated. Alternative embodiments will become apparent to those skilled in the art to which the present invention pertains without departing from its spirit and scope.

What is claimed is:

1. A method of reducing a fracture of a bone, the method comprising:
   coupling a bone plate to the bone with a first device inserted through the bone plate and into engagement with the bone on a first side of the fracture;
   inserting a compression screw through a hole in the bone plate and into engagement with the bone on an opposite side of the fracture to adjust the position of the bone and surrounding tissue, wherein the hole is configured for interchangeably receiving locking and compression screws and the hole includes a thread that makes a complete revolution around the hole;
   removing the compression screw from the hole and engagement with the bone; and
   inserting a locking screw into the hole and into engagement with the bone, wherein threads of the hole completely surround threads of a head of the locking screw.

2. The method of claim 1, wherein the position of the bone and surrounding tissue may be adjusted by insertion of the compression screw up to two millimeters in more than one direction.

3. The method of claim 1, wherein the first device is a compression screw.

4. The method of claim 1, wherein the first device is a locking screw.

5. The method of claim 1, wherein the first device is a provisional fixation pin.

6. The method of claim 1, further comprising, prior to inserting the compression screw, inserting one or more provisional fixation pins through the bone plate and into engagement with the bone.

7. The method of claim 6, further comprising adjusting the one or more provisional fixation pins to draw a bone fragment to the bone plate.

8. The method of claim 7, further comprising providing a provisional fixation slot in the bone plate.

9. The method of claim 1, further comprising providing the hole with an unthreaded top portion and a threaded bottom portion.

10. The method of claim 9, wherein the top portion is configured to engage the head of a compression screw and the bottom portion is configured to engage a threaded head of a locking screw.

11. The method of claim 9, wherein the top portion and the bottom portion are tapered at different angles.

* * * * *